(12) United States Patent
Mewes et al.

(10) Patent No.: US 11,648,069 B2
(45) Date of Patent: May 16, 2023

(54) SYSTEM AND METHOD FOR TRACKING THE POSITION OF A TARGET OBJECT

(71) Applicant: Siemens Healthcare GmbH, Erlangen (DE)

(72) Inventors: Philip Mewes, Nuremberg (DE);
Gunter Mueller, Heroldsberg (DE);
Claus Seisenberger, Neufrannhofen (DE)

(73) Assignee: Siemens Healthcare GmbH, Erlangen (DE)

( * ) Notice: Subject to any disclaimer, the term of this patent is extended or adjusted under 35 U.S.C. 154(b) by 60 days.

(21) Appl. No.: 16/757,128

(22) PCT Filed: Sep. 19, 2018

(86) PCT No.: PCT/EP2018/075376
§ 371 (c)(1),
(2) Date: Apr. 17, 2020

(87) PCT Pub. No.: WO2019/081132
PCT Pub. Date: May 2, 2019

(65) Prior Publication Data
US 2020/0246088 A1 Aug. 6, 2020

(30) Foreign Application Priority Data

Oct. 27, 2017 (EP) .................... 17198926

(51) Int. Cl.
*A61B 34/30* (2016.01)
*A61B 34/20* (2016.01)
(Continued)

(52) U.S. Cl.
CPC ................ *A61B 34/30* (2016.02); *A61B 6/12* (2013.01); *A61B 34/20* (2016.02);
(Continued)

(58) Field of Classification Search
CPC . A61B 34/20; A61B 34/30; A61B 2034/2055; A61B 6/12; A61B 2090/376
See application file for complete search history.

(56) References Cited

U.S. PATENT DOCUMENTS

| 8,417,318 B2 | 4/2013 | West |
| 2007/0265527 A1 | 11/2007 | Wohlgemuth |

(Continued)

FOREIGN PATENT DOCUMENTS

| CN | 105078577 A | 11/2015 |
| EP | 1854425 A1 | 11/2007 |

(Continued)

OTHER PUBLICATIONS

European Office Action for European Application No. 17 198 926.2-1115 dated Oct. 8, 2019.
(Continued)

*Primary Examiner* — Chao Sheng
(74) *Attorney, Agent, or Firm* — Lempia Summerfield Katz LLC

(57) ABSTRACT

The disclosure relates to a system for tracking the position of a target object. A marker arranged on the target object and an additional control marker are tracked by a tracking device secured to the robot arm. The control marker is arranged in a known specified three-dimensional positional relationship with the tracking device. During the tracking of the position of the target object, the specified three-dimensional positional relationship between the tracking device and the control marker is measured. In the event of a difference between the measured and the real specified three-dimensional positional relationship, a corresponding signal is generated depending on the difference.

17 Claims, 3 Drawing Sheets

(51) Int. Cl.
  *A61B 6/12* (2006.01)
  *A61B 90/00* (2016.01)
  *A61B 17/00* (2006.01)
(52) U.S. Cl.
  CPC .............. *A61B 2017/00119* (2013.01); *A61B 2034/2055* (2016.02); *A61B 2090/376* (2016.02)

(56) References Cited

U.S. PATENT DOCUMENTS

| | | | |
|---|---|---|---|
| 2007/0270690 A1 | 11/2007 | Woerlein | |
| 2012/0259464 A1* | 10/2012 | Morioka | B25J 9/1674 700/254 |
| 2013/0325182 A1* | 12/2013 | Setrakian | B25J 9/161 700/264 |
| 2013/0345718 A1* | 12/2013 | Crawford | A61B 34/70 606/130 |
| 2014/0188132 A1 | 7/2014 | Kang | |
| 2015/0327948 A1 | 11/2015 | Schoepp et al. | |
| 2016/0258782 A1 | 9/2016 | Sadjadi | |
| 2017/0245946 A1 | 8/2017 | Tabandeh et al. | |

FOREIGN PATENT DOCUMENTS

| | | |
|---|---|---|
| EP | 1891895 A1 | 2/2008 |
| EP | 2732765 A1 | 5/2014 |
| WO | WO2007003949 A1 | 1/2007 |
| WO | WO2010049834 A1 | 5/2010 |
| WO | WO2016168671 A1 | 10/2016 |

OTHER PUBLICATIONS

European Search Report for European Application No. 17198926.2-1115 dated Mar. 1, 2018.

International Search Report and the Written Opinion for International Patent Application PCT/EP2018/075376 dated Nov. 2, 2018.

* cited by examiner

ND METHOD FOR TRACKING
THE POSITION OF A TARGET OBJECT

The present patent document is a § 371 nationalization of PCT Application Serial No. PCT/EP2018/075376, filed Sep. 19, 2018, designating the United States, which is hereby incorporated by reference, and this patent document also claims the benefit of European Patent Application No. 17198926.2, filed Oct. 27, 2017, which is also hereby incorporated by reference.

TECHNICAL FIELD

The disclosure relates to a system, in particular a robotic system, and a method for tracking a position of a target object. The system or method may be used in a medical environment, for example, in minimally invasive surgery. In this case, the target object may be a patient to be treated or examined.

BACKGROUND

It is known from practice to arrange a marker on the patient and, on the basis of this marker, to track the position of the patient by a navigation system, which may include a camera directed at the marker. Following registration, (for example, with image data of the patient generated by an X-ray system), this enables a location-specific superimposition to be displayed, (for example, as an overlay), on a medical screen in real time even when the patient moves. In particular, when using additional tools or devices, space may be quickly become tight. In addition, it may require a significant amount of effort to monitor the respective spatial positional relationships between all the movable devices and objects involved and to keep them consistent with one another.

SUMMARY AND DESCRIPTION

It is the object of the present disclosure to enable tracking of a position of a target object with improved reliability in a particularly simple manner.

The scope of the present disclosure is defined solely by the appended claims and is not affected to any degree by the statements within this summary. The present embodiments may obviate one or more of the drawbacks or limitations in the related art.

A system, (e.g., a robotic system), includes a robot with a movable robot arm, a tracking device, and a data processing device. The tracking device is configured to track the position of a target object, (in particular, a patient), on the basis of a marker arranged on the target object by processing data provided by the tracking device and/or the marker by the data processing device of the system. In order to enable the tracking of the position of the target object, in a particularly simple and space-saving manner, the tracking device is secured, at least indirectly, to the robot arm. In order to achieve improved reliability during the tracking of the position of the target object, the system additionally includes at least control marker arranged in a specified, e.g., known in the operation of the robot, spatial positional relationship with the tracking device.

In an embodiment, the control marker is arranged in a spatial positional relationship with the tracking device that is constant during the operation of the robot. In a development, the control marker is secured, at least indirectly, to the robot arm. Like the control marker, at least during the operation of the robot or the movement of the robot arm, the tracking device may also be secured to, (e.g., arranged on), the robot arm in a constant specified spatial positional relationship to the robot arm.

The system is configured to measure or determine the spatial positional relationship between the tracking device and the control marker, in particular continuously or regularly during the tracking of the target object. The system is furthermore configured to compare the measured spatial positional relationship with the real specified spatial positional relationship between the tracking device and the control marker. Therefore, this specified spatial positional relationship is known because a respective position of both the tracking device and the control marker relative to one another may be ascertained from their arrangement on the robot arm, for example, before the system is used, for example from or on the basis of a system specification or by a corresponding independent measurement and/or calibration, and, during use of the robotic system, may remain constant at least on a movement of the robot arm. The system is furthermore configured, in the event of a difference being identified between the measured and the real specified spatial positional relationship, to generate a corresponding signal in dependence on the difference, in particular to output it as a control signal. Therefore, the difference identified may be a result of the comparison of the measured and the specified spatial positional relationships.

Therefore, the present system advantageously represents an integrated system in which the tracking device, which may correspond to a part of conventional independent navigation systems, is integrated with the robot by being arranged on the robot arm, (e.g., may form a common device or system). Hence, there is advantageously no dependence on an additional, separate, external navigation system. As a result, incompatibilities may be avoided in a particularly simple manner and/or there is no need for additional effort, for example, to develop or adapt an individual one-off solution for the respective system.

The fact that the tracking device is secured to the robot arm may mean that during the operation, (e.g., during the use or movement), of the robot, the robot arm and the tracking device may move together as a rigid system. As a result, there is advantageously no need for separate tracking of the tracking device, as may conventionally be necessary when using a navigation system embodied as an independent separate device. It is also possible to achieve an improved workflow because, for example, the probability of the view being obscured between the tracking device and the marker may be reduced because the robot arm is aligned in the direction of the patient and hence the problem of the robot arm arriving at a position between the marker arranged on the patient and a tracking device of a separate navigation system may be eliminated.

The robot may be a medical robot or an industrial robot with at least six, (e.g., six to ten), axes or degree of freedom. Such robots include corresponding controls and/or sensors, which are able to monitor the respective current position and orientation, e.g., the pose, of the robot and provide corresponding position data. The system may also include a C-arm device, for example. Herein, the C-arm may be movable and thus may be a robot or robot arm. In this case, it may be possible to arrange the tracking device on the C-arm. The control marker and/or a further marker, (for example, an auxiliary marker), may be arranged on or secured to the C-arm or a patient support in a known spatial positional relationship with the C-arm or the tracking device.

Therefore, because the position data is already available when the robot is used, the known positional relationship between the tracking device and the robot arm advantageously enables a separate sensor system or separate monitoring of the position and orientation of the tracking device to be dispensed with.

The fact that the constant specified spatial positional relationship of the control marker and/or the tracking device relative to the robot arm exists or is present during the operation of the robot, means, or at least does not preclude, that, for example during a stoppage of the robot—and hence also of the robot arm—the respective position and/or orientation of the control marker and/or the tracking device may be changed or adjusted. Therefore, the securing to the robot arm may be reversible and may be released non-destructively.

Similarly to the marker, the control marker may also be embodied in various ways. For example, the control marker may be dependent upon or tuned to the type or embodiment of the tracking device. If the tracking device is embodied for optical tracking, (e.g., as a camera), the marker and the control marker may be embodied as reflective metallic or plastic spheres or hemispheres. Herein, optical tracking does not have to be restricted to the use of visible light, but may use infrared light or other frequencies or wavelengths just as effectively. If the tracking device is embodied for electromagnetic tracking (EMT), the marker and the control marker may include at least one, (e.g., more than one), receiver coils or electromagnetic sensors. Herein, the tracking device may include an arrangement of a plurality of transmitter coils, (for example, eight transmitter coils). Herein, these transmitter coils may be arranged in a known spatial positional relationship with respect to one another in order to enable reliable tracking independently of any specific orientation. Herein, the individual transmitter coils may be activated in a specified sequence, e.g., send out a respective tracking signal in a specific order. Together with the known arrangement of the transmitter coils, this enables the spatial positional relationship between the tracking device and the marker or the control marker to be ascertained from a signal received or measured on the marker or on the control marker and hence therefore to determine the position and orientation of the marker or the control marker.

In any case, the tracking device on the one hand and the marker or control marker on the other may be tuned or configured to one another such that their interaction enables the tracking. In order to minimize effort and enable the tracking to be checked or the reliability thereof to be monitored, (e.g., to enable the determination of the position of the marker and hence the target object), the marker and the control marker may be of the same type. The tracking device and the marker or the control marker and/or the data processing device, (e.g., the system as a whole), may be configured to determine the respective position and location in three spatial position coordinates and three spatial angles (6D tracking). Thus, it is advantageously possible to determine not only the position of the target object, but also the orientation thereof, e.g., the respective pose overall.

The data processing device may include a processor device, (for example, a microchip or microcontroller), and a data memory. This data memory may be used to buffer the data provided by the tracking device and/or the marker and/or the control marker. Program code that represents or encodes method acts of the method may also be stored in the data memory. Therefore, the data processing device and hence the system may be configured to execute the program code in order to carry out the method by the processor device. The data processing device may be arranged in a centralized manner, e.g., monolithically, such as in or on the robot or in a separate housing. It may be connected to the robot via a data connection or a data line. However, the data processing device can also have a distributed arrangement, e.g., it may be composed of components arranged at different locations. The data processing device or a part thereof may also, for example, be a computer or a control device, which may be used for other tasks at the same time. The data processing device may be coupled to a display or visualization device in order, for example, to depict the tracked position of the target object. Here, it is also, for example, possible to visualize the current reliability or quality of the tracking or the ascertained position and/or orientation of the target object.

One particular advantage of the present disclosure is that the comparison result of the comparison of the specified spatial positional relationship with the corresponding measured spatial positional relationship between the tracking device and the control marker enables the reliability or quality of the tracking, e.g., the determination of the position of the target object or the marker. Due to the constant specified spatial positional relationship, it is to be expected with operation as intended and without problems that the position of the control marker relative to the tracking device, e.g., the distance between them, will provide a constant signal or measurement result. Therefore, if a deviation or difference from this expected constant signal or measurement result is measured or established during operation, then this is a direct and reliable indication that there is a fault. In such a case, it then has to be expected that the measured position of the target object may also deviate from its actual position accordingly. It is particularly with electromagnetic tracking that faults or inaccuracies may be caused in a non-obvious or directly identifiable way, for example, by metallic objects in the region of the marker or by electromagnetic interference fields emanating from other devices.

Therefore, the present disclosure may advantageously indicate the reliability of the tracking of the target object without an additional device and with a minimal space requirement and hence contribute to an improved treatment outcome. Because the same tracking device is used to measure the spatial positional relationship between the tracking device and the control marker, e.g., to track the control marker, as that used to track the marker or the target object, this advantageously also enables malfunctions or disruptive influences on the tracking device to be identified directly. Therefore, overall, the simultaneous integration of the tracking device and the redundant control marker in or on the system advantageously implements a quality check or monitoring of reliability that is able to quantitatively detect and indicate or provide feedback on any faults in the tracking device, the tracking or generally in the environment of the system.

During operation of the system, (e.g., in a working position), the control marker may be located in close proximity, (e.g., at a distance of less than 1 m or at a distance of less than 50 cm), from the marker on the target object. This may be achieved in that the control marker is arranged in a front, e.g., facing the target object, end region, such as on a tool held on the system or provided as part of the system. This advantageously enables disruptive influences acting on or in the region of the marker to be identified particularly reliably, in particular even if they have a correspondingly short spatial range.

Hereinafter, for purposes of clarity, the system is also referred to as a robotic system without any restriction.

In a further advantageous embodiment, the tracking device may be secured to a robot flange of the robot arm or to a foot of the robot arm, e.g., a robot foot of the robot. The robot foot may form an end of the robot arm facing away from the target object and, for example, be fixed or mounted on a floor of a respective operating area of the robotic system. On the other hand, the robot flange may be arranged on an opposite end of the robot arm facing the target object. A tool provided for interaction with the target object may become or be secured to the robot flange, for example. The robot flange or the tool may also form an end of the robot arm. Securing the tracking device to the robot flange has the advantage that, when the robotic system is in use, the tracking device is automatically aligned with the target object and is or may be brought particularly close to the target object and hence to the marker. The shorter distance between the tracking device and the marker associated therewith may advantageously enable more precise tracking of the target object. In particular, electromagnetic tracking has a limited effective range. However, even when using optical tracking, due to the closer proximity to the target object, securing or arranging the tracking device on the robot flange may minimize the probability of disruptive objects entering the line of sight between the tracking device and the marker. On the other hand, securing or arranging the tracking device on the robot foot may have the advantage that it does not occupy any space in the immediate vicinity or environment of the target object, for example, provides more freedom of movement for an attending physician.

In an advantageous development, the tracking device includes an electromagnetic field generator (EM field generator), e.g., one or more transmitter coils. The control marker—and, in some examples, also the marker—includes a sensor tuned to the EM field generator, in particular at least one receiver coil. Therefore, in this development, electromagnetic tracking is used to track the position of the target object and to measure the spatial positional relationship between the tracking device and the control marker. Electromagnetic tracking may advantageously be less susceptible to interference from objects entering the direct line of sight between the tracking device and the control marker or the marker on the target object than optical tracking.

In an advantageous development, the tracking device includes a camera for optically detecting the marker and the control marker. Therefore, in this development, optical tracking is used to track the position of the target object and to measure the spatial positional relationship between the tracking device and the control marker. Herein, the control marker and/or the marker on the target object may include a plurality of characteristics or features which may be detected optically by the tracking device and which enable the respective orientation in space to be determined. Herein, the control marker and/or the marker may include a respective ensemble of a plurality of partial markers arranged in a known fixed spatial positional relationship to one another. Optical tracking may advantageously enable reliable tracking or measurement of the respective positions or spatial positional relationships over larger spatial distances than is, for example, possible with electromagnetic tracking. Compared to electromagnetic tracking, the use of optical tracking may also reduce susceptibility to interference from electromagnetic influences and/or for example metallic objects that enter the vicinity of the control marker and/or the marker.

In an advantageous development, the tracking device and/or the control marker is secured movably but fixably to the robot arm in order to specify their spatial positional relationship with respect to one another. In other words, it is therefore then possible for the location and/or orientation of the tracking device and/or the control marker relative to the robot arm to be adjusted or set and then fixed in a new position and orientation. For this purpose, the tracking device and/or the control marker may be secured to the robot arm by a lockable swivel arm or articulated arm. This advantageously enables it to be provided in accordance with requirements that both the control marker and the marker are located, e.g., may be arranged, on the target object in a visual or detection range of the tracking device. If the tracking device or the control marker is adjusted or realigned while the robot arm and the target object are at rest, it is advantageously possible for an automatic re-registration or new registration to be performed. Therefore, this enables the new spatial positional relationship between the tracking device and the control marker, e.g., the respective new position and/or orientation, to be ascertained automatically and taken into account for further tracking of the position of the target object performed after the respective fixing and when measuring the new spatial positional relationship that is then specified between the tracking device and the control marker. Here, it is, for example, possible for the data supplied by the tracking device and/or the control marker and/or the marker to be registered with image data of an imaging system, for example, an X-ray device. Therefore, compared to conventional systems, the present disclosure has the advantage of improved flexibility and simplified handling because, due to the known specified spatial positional relationship, sufficient information to enable the re-registration to be performed automatically on a realignment of an element, (e.g., the tracking device or the control marker), is automatically available.

In an advantageous development, the robotic system additionally includes an external ensemble of auxiliary markers, in particular secured to neither the robot nor the target object. Herein, the robotic system is configured to measure a spatial positional relationship between the tracking device and the ensemble of auxiliary markers and/or a spatial positional relationship of the auxiliary markers with respect to one another, (e.g., relative to one another), when tracking the position of the target object and to check the plausibility of the tracking of the position of the target object on the basis of a corresponding measurement result. The auxiliary markers may also be embodied like the control marker or like the marker on the target object.

The plausibility checking of the tracking of the position of the target object, (e.g., the ascertained position and orientation of the target object), may include or mean comparing the measured spatial positional relationship of the auxiliary markers or with the auxiliary markers with the corresponding measured value or measurement result expected in the cause of trouble-free operation. For the plausibility checking, it is also possible to check whether there is a deviation or difference between the measured and the expected value or signal that is greater than a specified threshold value. This threshold value may be called an interference threshold value.

The auxiliary markers may be arranged with respect to one another, (e.g., relative to one another), in a known fixed positional relationship. This may enable an unambiguous determination of the orientation of the ensemble of auxiliary markers in space, e.g., from every viewing direction or perspective. The auxiliary markers may be or become positioned differently, for example, fixed relative to the robot or relative to the target object and/or fixed, (e.g., positionally stable), in an external coordinate system, which may be defined by the walls, floor, and ceiling of an operational area in which the robotic system is located.

The use of the additional auxiliary markers and their known spatial position and location advantageously enables improved flexibility and quality of the tracking of the target object and the determination of the reliability of this tracking to be achieved. Similarly to the case described in connection with the control marker, with trouble-free operation of the robotic system, a signal or measurement result known in advance is to be expected for the spatial positional relationship between the tracking device and the auxiliary markers and/or for the spatial positional relationship of the auxiliary markers with respect to one another. In the former case, this may be a signal that changes in a specific expected manner and, in the latter case, a specific constant signal or measurement result with a constant variable. If a deviation from this is then identified during operation, it may be concluded that there is a fault or limited accuracy or reliability during the tracking of the position of the target object. If, on the basis of the auxiliary markers, such a deviation or difference is determined by a corresponding comparison, e.g., a fault is identified, the data processing device may also automatically generate or output a corresponding signal or control signal.

The use of the ensemble, e.g., of the plurality of auxiliary markers, advantageously enables it to be provided that at least one auxiliary marker or more than one of the auxiliary markers is/are in the field of view or detection range of the tracking device over a particularly large swivel or movement range of the robot arm. Therefore, on a movement of the robot arm, over a period of time, individual auxiliary markers may enter and/or leave the detection range of the tracking device. It is also possible for this time period when the auxiliary markers enter or leave the detection range of the tracking device—and/or the corresponding entry and/or exit times—to be, for example, automatically evaluated by the data processing device in order to check or evaluate the tracking of the target object, e.g., in other words to identify faults. Herein, it may be particularly advantageous for the individual auxiliary markers of the ensemble to have respective identification features on the basis of which they may be identified unambiguously and individually by the tracking device and/or by the data processing device. Herein, the ensemble of auxiliary markers may include a plurality of groups of auxiliary markers that are arranged in a spatially distributed manner. In each group of auxiliary markers, the respective auxiliary markers may be arranged relative to one another in such a way that an unambiguous determination of the spatial orientation of this group of auxiliary markers is enabled from every viewing direction.

Additionally or alternatively to the auxiliary markers, one or more additional tracking devices may be provided in a corresponding manner. This, for example, enables the control marker to be tracked from a known alternative perspective. Therefore, this provides additional redundancy, which may improve the reliability of the tracking of the target object and/or the reliability of the identification of faults and flexibility when arranging and/or aligning the robot arm and/or the tracking device arranged on the robot arm.

The method is used to track the position, in particular the position and orientation of a target object, (e.g., a patient), by a system, (e.g., a robotic system). Herein, the position of the target object is tracked by a tracking device secured to a movable robot arm of a robot and a marker arranged on the target object. In a further method act, during the tracking, a spatial positional relationship between the tracking device and at least one control marker in a known specified, (e.g., constant), spatial positional relationship with the tracking device during the operation of the robot is measured. The control marker may also be secured to or arranged on the robot arm. In a further method act, this measured spatial positional relationship is compared with the corresponding real specified spatial positional relationship. If a difference is identified between the measured and the real specified spatial positional relationship, in a further method act, the system generates a corresponding signal in dependence on the identified difference. Therefore, the method may be performed by a robotic system.

In an advantageous development of the method, the signal is output as a control signal.

In an advantageous development of the method, a warning about the identified difference is output in response to the signal or the control signal. Therefore, the signal may be a control signal for a warning device and may be correspondingly output or transmitted to the warning device in order to induce this to output the warning, (e.g., an acoustic and/or visual warning). A fault, a loss, or a reduction in accuracy or reliability during the tracking of the position of the target object may not be readily identified by a respective user or operator. The warning may advantageously draw the attention of the user, (for example, an attending physician), to this. This advantageously enables the possibility to be avoided of a respective user unquestionably relying on the robotic system or the position tracking of the target object even if there is a fault. Therefore, the method, in particular the warning, may help to avoid errors or complications during the treatment of the patient.

In an advantageous development of the method, following a change to the specified spatial positional relationship between the tracking device and the control marker, in which either the tracking device or the control marker is adjusted, the system automatically performs a registration or re-registration with a specified coordinate system or corresponding image data, in particular of a imaging system. Herein, the registration is performed on the basis of the non-adjusted control marker or on the basis of the non-adjusted tracking device or corresponding measured and/or known position data. Herein, the change to the specified spatial positional relationship is made during a stoppage, in particular relative to the target object, of the robot arm. This provides that only one element or one variable within the overall system including the robotic system and the target object is changed thus enabling the re-registration necessitated thereby to be carried out particularly easily and with little effort. Therefore, this procedure advantageously makes it possible to react flexibly to situation-related circumstances in order, for example, to provide that the control marker and the marker arranged on the target object remain in the field of view or detection range of the tracking device even in the event of future movements of the robot arm.

In an advantageous development of the method, a correction value is determined from the identified difference. This correction value is then automatically taken into account during the tracking of the position of the target object in order to compensate for a disruptive influence responsible for the difference. Thus, for example, the real position and location of the target object may be visualized or displayed with improved reliability, in particular under a wide variety of conditions. Therefore, the signal may be a control signal for a display device or for a device that generates or controls the visualization of the position and location of the target object. Therefore, the correction value may be treated or interpreted as an offset so that the control signal may then induce a corresponding displacement and/or rotation of the visualization or depiction of the target object or the position thereof in accordance with the correction value.

Therefore, the signal may be output as a control signal to an external device or an external unit. However, the signal may also be an internal signal, e.g., sent, that is to say transmitted, to an internal functional unit of the robotic system or the data processing device. The latter may be the case if the device is used to visualize the target object or the spatial position of the target object is part of the robotic system.

The properties and developments of robotic system and of the method disclosed above and in the following and the corresponding advantages are in each case mutually transferrable between these aspects of the present disclosure. This also applies to components and devices that are or may be used to carry out the method. Therefore, the disclosure also includes developments of the robotic system and of the method with embodiments that are not explicitly described here in the respective combination.

BRIEF DESCRIPTION OF THE DRAWINGS

Further features, details, and advantages will emerge from the following description of exemplary embodiments and with reference to the drawings, in which.

DETAILED DESCRIPTION

In the exemplary embodiments, the described components of the embodiments in each case represent individual features of the disclosure to be considered independently of one another, which in each case also develop the disclosure independently of one another and hence should also be regarded as part of the disclosure individually or in a combination other than that shown. Furthermore, the described embodiments may also be supplemented by further features of the disclosure that have already been described.

Figure 1:
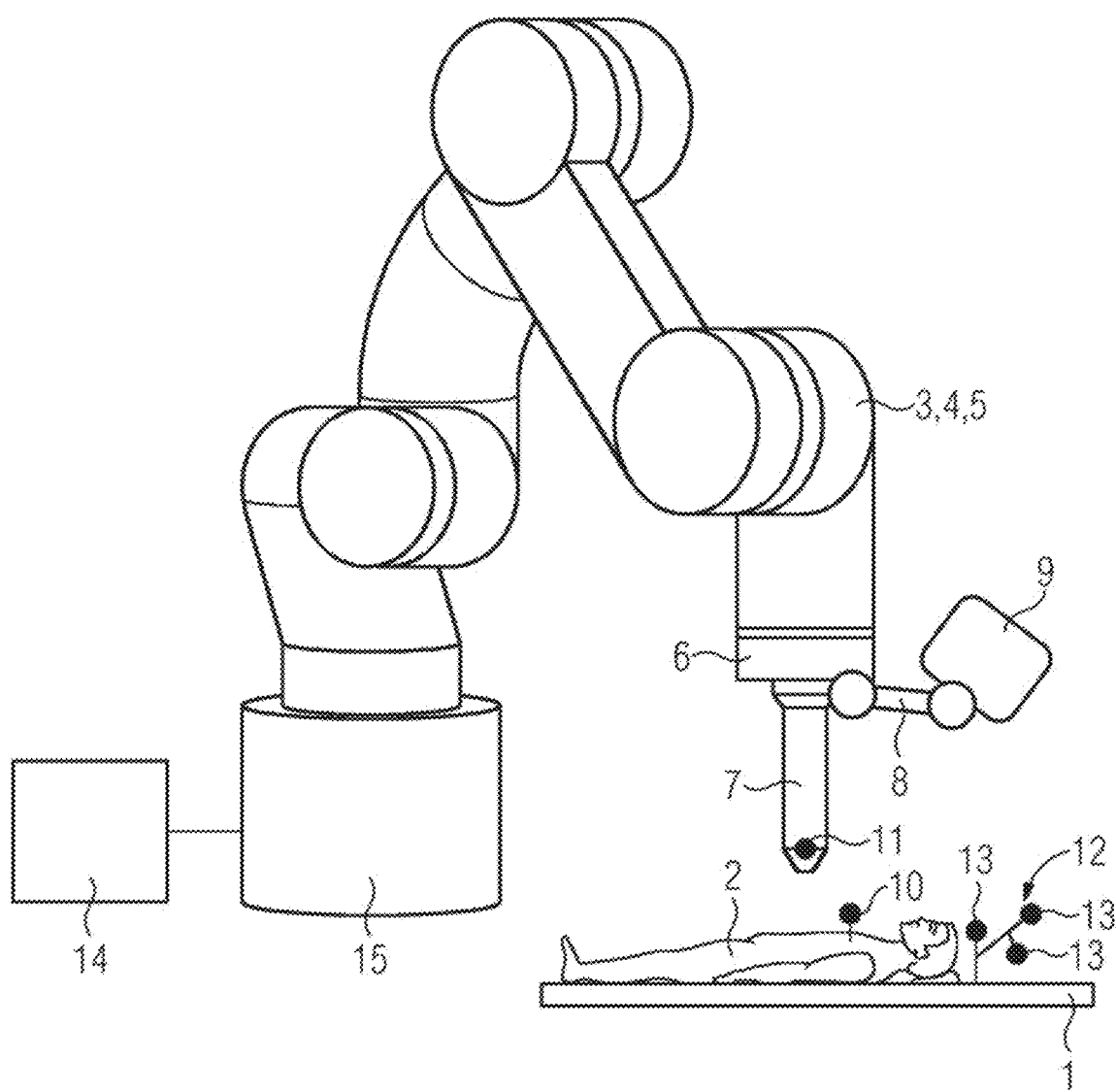
FIG. 1 depicts a schematic side view of an example of a robotic system with a tracking device when used on a patient.

FIG. 1 shows a schematic side view of a treatment situation. Here, a patient 2 being treated or to be treated by a robotic system 3 lies on a patient support 1. In the present case, the robotic system 3 includes a robot 4 with a movable, multi-axis robot arm 5. On one end of the robot arm 5, there is a robot flange 6 via which a tool 7 is secured to the robot arm 5. Furthermore, a tracking device 9 is secured to the robot flange 6—and hence at least indirectly to the robot arm 5—via an articulated arm 8. However, herein the robot flange 6 and/or the tool 7 may also be part of the actual robot arm 5. The tracking device 9 may include an EM field generator and/or a camera, (e.g., a stereoscopic camera). The tracking device 9 is used to track a position and orientation of the patient 2.

For this purpose, in the present case, a marker 10 is arranged on the patient 2. The tracking device 9 is configured such that the marker 10 is located in its detection range. The robotic system 3 additionally includes a control marker 11, which in the present case is located on a tip of the tool 7. However, the control marker 11 may also be arranged directly on the robot arm 5 or, for example, on the robot flange 6. Instead of the direct arrangement shown here, the control marker 11 may also be connected similarly to the tracking device 9 via an articulated arm. The tracking device 9 and the control marker 11 are located in a known constant specified spatial positional relationship with respect to one another and with the robot arm 5. On the other hand, the spatial positional relationship between the tracking device 9 and the marker 10 may change on a movement of the actual robot arm 5. It is provided that the control marker 11 is also located in the detection range of the tracking device 9.

In addition, an ensemble 12 of auxiliary markers 13 is provided here, in the present case, by way of example on the patient support 1 in the vicinity of the patient 2. Hence, in the present case, the auxiliary markers 13 are located in a fixed spatial positional relationship with the marker 10 and hence with the patient 2. The auxiliary markers 13 are also in a known fixed spatial positional relationship relative to one another. Like the marker 10 and the control marker 11, the auxiliary markers 13 may also be detected by the tracking device. Herein, due to the arrangement of the auxiliary markers 13, the location and orientation of the ensemble 12 may be determined unambiguously from every perspective of the tracking device 9. During the treatment, e.g., during the use of the robotic system 3, the ensemble 12 may be permanently or only temporally located completely or partially in the detection range of the tracking device 9.

Signals or data generated by the tracking device 9, the marker 10, the control marker 11, and/or the auxiliary markers 13 may be processed by a data processing device 14 of the robotic system 3. From these signals or data, the data processing device 14 may, (for example, in a specified coordinate system), calculate respective absolute and/or relative positions and orientations of the tracking device 9, the marker 10 and hence the patient 2, the control marker 11 and the ensemble 12. Hence, therefore, the position or spatial location of the robot arm 5, in particular the tool 7, relative to the patient 2 may be determined and tracked.

Figure 2:
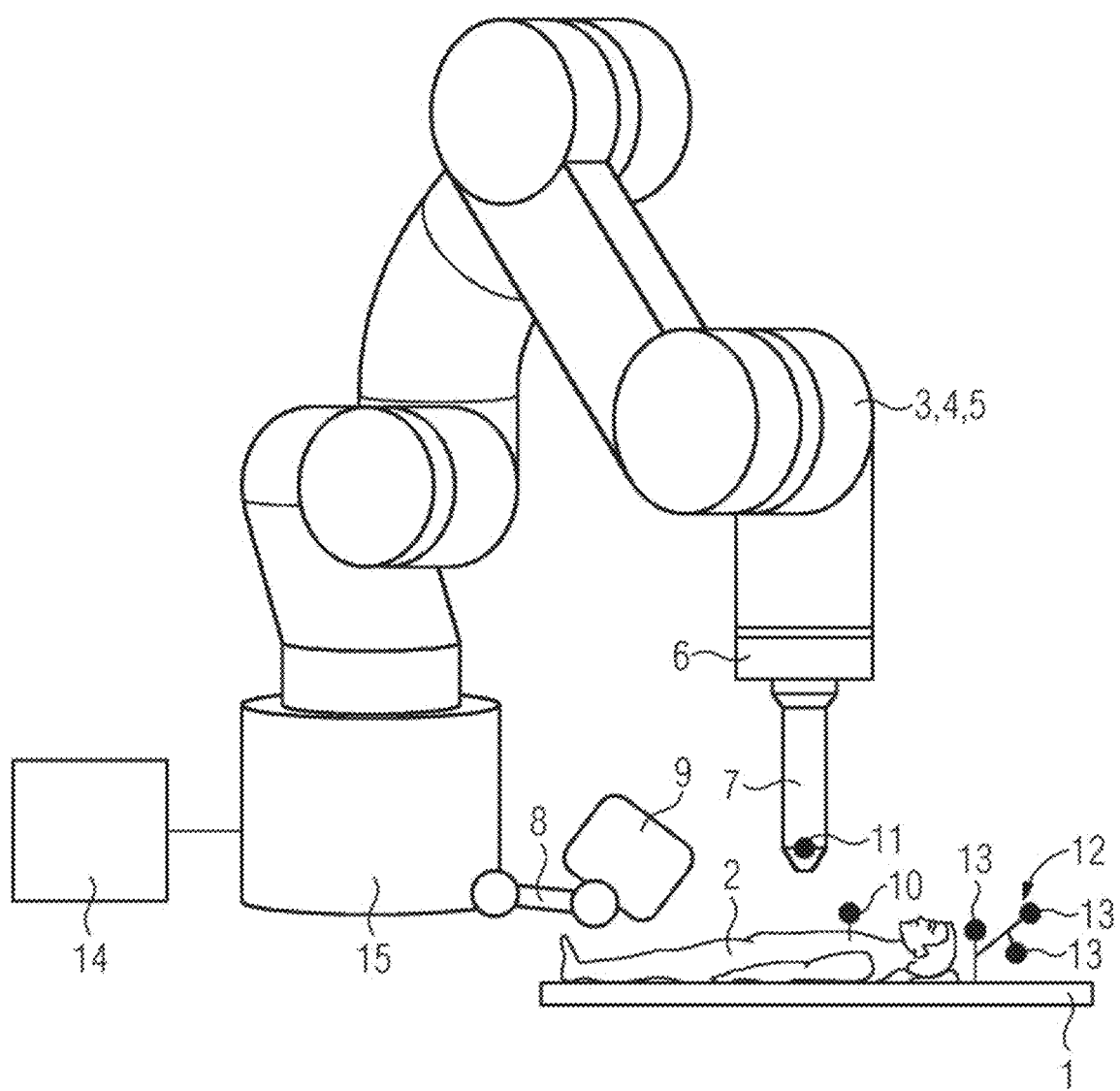
FIG. 2 depicts a schematic side view of the situation in FIG. 1, wherein the tracking device is arranged elsewhere on the robotic system.

FIG. 2 shows the same schematic side view as FIG. 1 with the difference that here the tracking device 9 is secured not to the robot flange 6, but to a foot 15 of the robot 4. This may entail an alternative embodiment of the robotic system 3. However, the tracking device 9 may be merely remounted on the same robotic system 3 in order, for example, to circumvent a spatial restriction, for example, by a further device that is not shown here.

Figure 3:
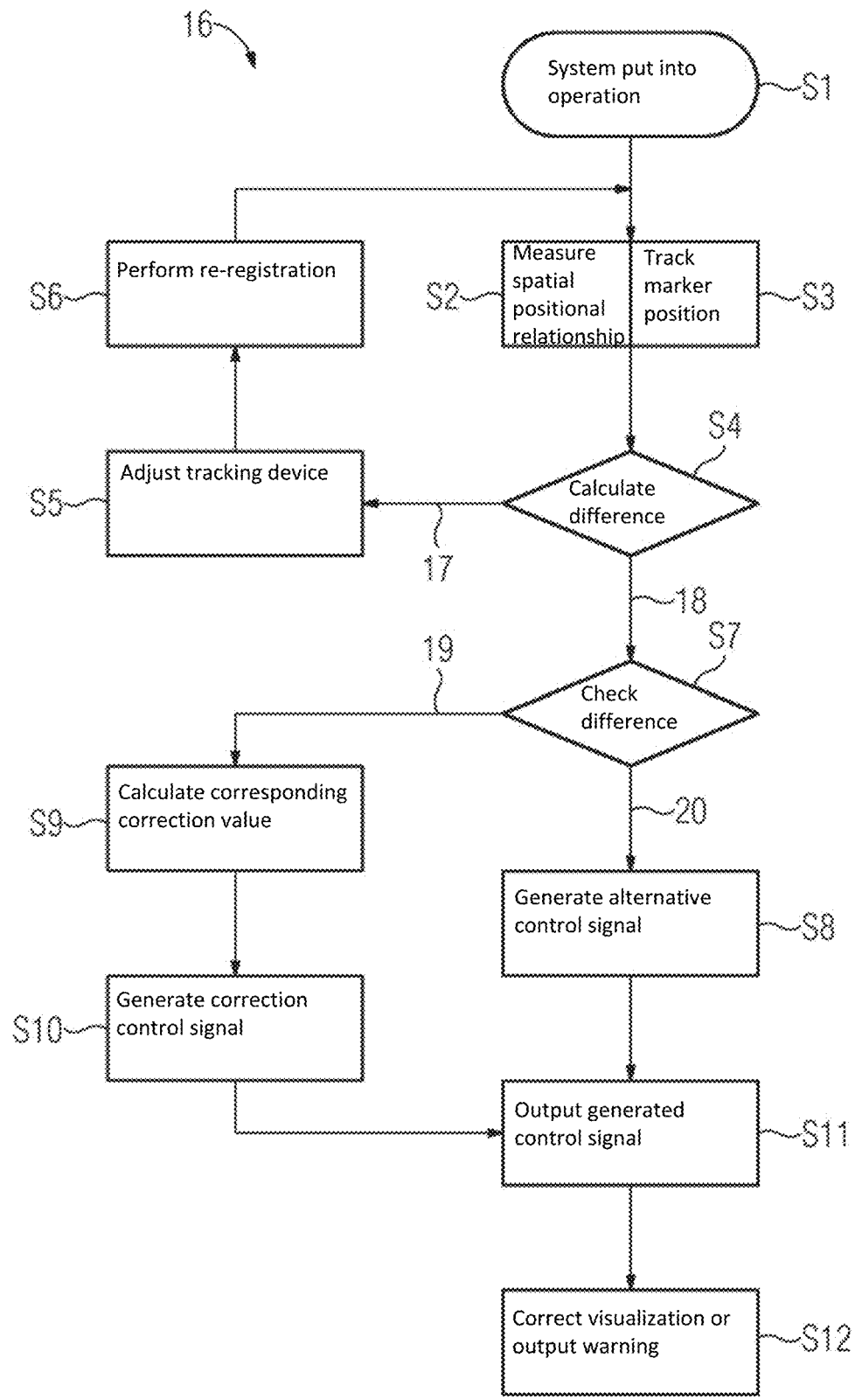
FIG. 3 depicts an exemplary schematic flowchart of a method for tracking the position of a target object.

FIG. 3 shows an exemplary schematic flowchart 16 of a method for tracking the position and orientation of a target object, (for example, the patient 2), in particular relative to the robotic system 3.

The following explains the method on the basis of FIG. 3 and with reference to FIG. 1 and FIG. 2. The method may begin with a method act S1. Here, the tracking device 9 and the ensemble 12 may be in a specified position. The specified or ascertained spatial positional relationships between the tracking device 9 and the control marker 11 and between the ensemble 12 and the marker 10 and/or, (for example, between the ensemble 12 and the foot 15), may be determined and are hence available as known variables in the method. It is also possible for the necessary registrations to be carried out, for example, of the marker 10 with the patient 2 or with image data or a coordinate system of an imaging system not shown here, for example, an X-ray system. For this purpose, corresponding X-ray images may be recorded and the position of the marker 10 in the X-ray images may be evaluated. Additionally or alternatively, a marker frame that is not shown here may be arranged in a specified manner on or around the patient 2 or on the imaging system 2. Finally, the robotic system 3 may be put into operation in method act S1.

In a method act S2, the specified, and hence known per se, spatial positional relationship between the tracking device 9 and the control marker 11 and possibly the ensemble 12 may be measured by the robotic system 3, e.g., by the system itself. For example, in parallel thereto, the determination of the position and the tracking of the position of the marker 10, e.g., of the patient 2, may be started in a method act S3.

In a method act S4, it is possible to calculate, for example, by a corresponding comparison, a difference between the spatial positional relationship or positional relationships measured in method act S2 and the specified respective value, e.g., which is also the expected measurement result in trouble-free operation. If the calculated difference is below a specified threshold value, the robotic system 3 and the tracking of the position of the patient 2 are functioning correctly, e.g., with sufficient reliability and/or accuracy. The treatment of the patient 2, e.g., the use of the robotic system, may then be commenced or continued. Therefore, the measurement or monitoring of the spatial positional relationship between the tracking device 9 and the control marker 11 is used to provide the integrity of the position measurement and tracking of the marker 10 and hence the patient 2.

During the treatment or during the method, it is then, for example, possible to follow a path 17 to a method act S5. Here, the tracking device 9 may be adjusted to a different position or remounted, as shown, for example, in FIG. 2 in comparison with FIG. 1. Herein, the tracking device 9 is fixed in its new position or orientation after the adjustment or remounting and is then also again in a constant, specified spatial positional relationship with the control marker 11. The adjustable arrangement or fixability of the tracking device 9 and/or the control marker 9 advantageously enables the elimination or circumvention of line-of-sight problems, e.g., obscured views or obstacles that would hinder the respective tracking or measurement. In contrast to conventional methods in which a separate navigation system is used, in the present case there is the advantage that the adjustment of the tracking device 9 and/or the control marker 11 may be performed on the actual device—e.g., here directly on the robotic system 3 or the robot 4—that is being operated by the user, for example, the attending physician and is in the range thereof. This advantageously enables an optimized, particularly efficient workflow.

In a method act S6, it is then possible for a re-registration to be performed automatically in order to take account of the new relative position of the tracking device 9.

The robotic system 3 may then be used as before, as indicated here by a loop back to method acts S2 and S3. Therefore, method acts S2 and S3 may be executed continuously during the use of the robotic system 3.

If it is identified in method act S4 that the difference is greater than the specified threshold value, a path 18 may be followed to a method act S7. In this act, a check may be performed as to whether it is possible to compensate for the difference identified, e.g., whether it is possible to calculate a correction value that may be taken into account during the tracking of the position and location of the patient 2 in order to compensate for a fault responsible for the difference, (for example, by the data processing device 14). If this is the case, a path 19 is followed to a method act S9 in which the corresponding correction value is calculated. This may require a previous calibration, which may also be performed in method act S1.

In a following method act S10, a correction control signal may then be generated on the basis of the calculated correction value, for example, for a visualization device that is not shown here.

If it emerges in method act S7 that it is not possible to compensate for the difference, the method may follow a path 20. This may be the case if the difference is too great, e.g., above a specified correction threshold value, and/or is, for example, subject to fluctuations, for example due to disruptive radio-frequency interference.

The path 20 is followed to a method act S8 in which an alternative control signal, e.g., different from the correction control signal, may be generated.

Regardless of whether path 19 or path 20 is followed, the respective control signal generated may be output in a method act S11. A respective output target, e.g., a device or functional unit on which the respective control signal is output, may be dependent thereupon or selected or determined in dependence on which control signal has been generated. Therefore, while the correction control signal generated in method act S10 may be output to a visualization device, the control signal generated in the method act S8 may be transmitted to a warning device for the output of a warning.

The reaction triggered or induced by the respective control signal may then take place in a method act S12. Therefore, this may be a correction to the visualization or depiction of the tracked position of the patient 2 and/or the output of the warning. Additionally or alternatively to the warning, it may advantageously be provided that the robot 3 or the robot arm 5 is stopped if the difference exceeds the specified threshold value and cannot be compensated for. This may advantageously prevent the robot arm 5, in particular the tool 7, being moved in a manner that cannot be checked by a respective user.

Overall, therefore, a robotic system 3 with integrated tracking is described in the present case. Herein, a distinction is made between the marker 10 arranged on the target object to be tracked, and the control marker 11, which is used exclusively for controlling or checking this tracking.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

Although the disclosure has been illustrated and described in greater detail by way of the exemplary embodiments, the disclosure is not restricted by way of the disclosed examples, and other variations may be derived therefrom by a person skilled in the art, without departing from the scope of protection of the disclosure.

The invention claimed is:

1. A system comprising:
   a data processing device;
   a robot with a movable robot arm;
   a tracking device at least indirectly secured to the robot arm, wherein the tracking device is configured for tracking a position of a target object based on a marker arranged on the target object by processing data provided by at least one of the tracking device or the marker by the data processing device; and at least one control marker additionally at least indirectly secured to the robot arm, wherein the at least one control marker is arranged in a specified fixed spatial positional relationship with the tracking device that is known and constant during an operation of the robot and movement of the robot arm, wherein the specified fixed spatial positional relationship is known based on a system specification, and wherein the system is configured to: measure a spatial positional relationship between the tracking device and the control marker during the tracking of the position of the target object, compare the measured spatial positional relationship with the specified fixed spatial positional relationship, generate a signal based on an identified difference between the measured spatial positional relationship and the specified fixed spatial positional relationship, and output a warning about the identified difference in response to the signal.

2. The system of claim 1, wherein the tracking device is secured to a robot flange or a foot of the robot arm.

3. The system of claim 1, wherein the tracking device comprises an electromagnetic field generator, and wherein the control marker comprises a sensor tuned to the electromagnetic field generator.

4. The system of claim 1, wherein the tracking device comprises a camera for optically detecting the marker and the control marker.

5. The system of claim 1, wherein the target object is a patient.

6. The system of claim 1, wherein the output of the warning indicates a fault or an inaccuracy in the tracking of the position of the target object.

7. The system of claim 1, wherein the system is further configured to:

determine a correction value from the identified difference; and generate and output a correction control signal based on the correction value in order to compensate for a disruptive influence responsible for the identified difference.

8. The system of claim 1, further comprising:

an external ensemble of auxiliary markers, wherein the system is configured to measure a spatial positional relationship between the tracking device and at least one of the external ensemble or the auxiliary markers with respect to one another and to check a plausibility of the tracking of the position of the target object when tracking the position of the target object based on a corresponding measurement result.

9. The system of claim 8, wherein the external ensemble of auxiliary markers is secured neither to the robot nor the target object.

10. A method for tracking a position of a target object by a robotic system, the method comprising:

tracking the position of the target object by a tracking device secured to a movable robot arm of a robot and a marker arranged on the target object;

measuring, during the tracking, a spatial positional relationship between the tracking device and at least one control marker at least indirectly secured to the robot arm and arranged in a specified fixed spatial positional relationship with the tracking device that is known and constant during an operation of the robot and movement of the robot arm, wherein the specified fixed spatial positional relationship is known based on a system specification;

comparing the measured spatial positional relationship with a corresponding specified fixed spatial positional relationship;

generating, by the robotic system, a signal based on an identified difference between the measured spatial positional relationship and the specified fixed spatial positional relationship in dependence on the identified difference; and outputting a warning about the identified difference in response to the signal.

11. The method of claim 10, wherein the signal is output as a control signal.

12. The method of claim 10, further comprising:

determining a correction value from the identified difference, wherein the correction value is taken into account during the tracking of the position of the target object in order to compensate for a disruptive influence responsible for the identified difference.

13. The method of claim 10, wherein the target object is a patient.

14. The method of claim 10, wherein the signal is generated when the identified difference is greater than a specified threshold value.

15. The method of claim 10, wherein, following a change to the specified fixed spatial positional relationship between the tracking device and the control marker made during a stoppage of the robot arm, with which one of the tracking device or the control marker is adjusted, the robotic system performs an automatic registration with a specified coordinate system, based on a non-adjusted control marker or a non-adjusted tracking device.

16. The method of claim 15, wherein the change to the specified fixed spatial positional relationship between the tracking device and the control marker made during the stoppage of the robot arm is relative to the target object.

17. The method of claim 15, wherein the robotic system performs the automatic registration with the specified coordinate system of an imaging system.

* * * * *